United States Patent
Zeng et al.

(10) Patent No.: US 12,144,891 B2
(45) Date of Patent: *Nov. 19, 2024

(54) BIODEGRADABLE DRUG ELUTING MICROSPHERE FOR THE TREATMENT OF SOLID TUMORS

(71) Applicant: Boston Scientific Scimed, Inc., Maple Grove, MN (US)

(72) Inventors: Hongxia Zeng, Maple Grove, MN (US); Steven Kangas, Woodbury, MN (US); Yen-Lane Chen, New Brighton, MN (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 616 days.

This patent is subject to a terminal disclaimer.

(21) Appl. No.: 16/597,122

(22) Filed: Oct. 9, 2019

(65) Prior Publication Data
US 2020/0093745 A1 Mar. 26, 2020

Related U.S. Application Data

(63) Continuation of application No. 14/986,774, filed on Jan. 4, 2016, now Pat. No. 10,471,012.

(60) Provisional application No. 62/099,719, filed on Jan. 5, 2015.

(51) Int. Cl.
*A61K 9/16* (2006.01)
*A61K 31/337* (2006.01)
*A61K 49/00* (2006.01)

(52) U.S. Cl.
CPC .......... *A61K 9/1647* (2013.01); *A61K 31/337* (2013.01); *A61K 49/0091* (2013.01)

(58) Field of Classification Search
None
See application file for complete search history.

(56) References Cited

U.S. PATENT DOCUMENTS

2014/0212355 A1 7/2014 Trollsas et al.

FOREIGN PATENT DOCUMENTS

WO WO-2006002365 A2 * 1/2006 ............... A61K 9/16

OTHER PUBLICATIONS

Saralidze et al (Polymeric Microspheres for Medical Applications. Materials 2010, 3, 3537-3564). (Year: 2010).*
Kilcup N et al., "Synthesis and evaluation of a pre-loaded drug eluting radiopaque composite embolic microsphere (CEM) for transarterial chemobembolization (TACE)", Journal of Vascular and Interventional Radiology, vol. 25, No. 3.
Tadic Z et al., "Piroxicam loaded PLGA microspheres for portal vein embolization", European Cells and Materials; Annual Meeting of the Swiss Society for Biomaterials, Swiss Society for Biomaterials, Switzerland, vol. 20, No. SUPPL. Jan. 11, 2010, p. 45.

* cited by examiner

*Primary Examiner* — Jake M Vu
(74) *Attorney, Agent, or Firm* — Seager, Tufte & Wickhem, LLP

(57) ABSTRACT

Polymer microspheres for embolizing blood vessels and optionally delivering therapeutic agents are provided.

12 Claims, 6 Drawing Sheets

BIODEGRADABLE DRUG ELUTING MICROSPHERE FOR THE TREATMENT OF SOLID TUMORS

CROSS-REFERENCE TO RELATED APPLICATIONS

This application is a continuation of U.S. patent application Ser. No. 14/986,774, filed Jan. 4, 2016, which claims priority under 35 U.S.C. § 119 to U.S. Provisional Patent Application Ser. No. 62/099,719 by Hongxia Zeng et al., filed Jan. 5, 2015. Each of the foregoing applications is hereby incorporated by reference in its entirety and for all purposes.

FIELD OF THE INVENTION

This application relates to the field of medical devices. More particularly, the application is related to devices and methods for the occlusion of blood vessels and/or the delivery of drugs to patients.

BACKGROUND

Embolization involves the partial or complete occlusion of blood vessels, limiting the flow of blood therethrough. The intentional occlusion of blood vessels ("therapeutic embolization") may be used to treat a variety of vascular and non-vascular conditions including cerebral and peripheral aneurysms, ateriovenous malformation, uterine fibroids and to reduce blood flow to solid tumors including liver tumors. Embolization may be achieved by any number of means, including through the use of polymer microspheres.

In a typical embolization procedure, local anesthesia is first given over a common artery. The artery is then punctured and a catheter is inserted and fluoroscopically guided into the area of interest. An angiogram is performed by injecting contrast agent through the catheter, thereby visualizing the portion of the arterial tree downstream of the distal end of the catheter. Once the catheter is positioned in a site where deposition of an embolic composition or agent is desired, the composition or agent is deposited through the catheter. The embolic agent is generally selected based on the size of the vessel to be occluded, the desired duration of occlusion, and/or the type of disease or condition to be treated, among others factors. Following delivery of the embolic agent to the site within the vessel to be occluded, a follow-up angiogram can be performed to determine the specificity and completeness of the occlusion.

Embolic microspheres are typically composed of synthetic polymers, including without limitation polyvinyl alcohol (PVA), acetalized PVA (e.g., Contour SE™ embolic agent, Boston Scientific, Natick, Mass., USA) and cross-linked acrylic hydrogels (e.g., Embospheres®, Biosphere Medical, Rockland, Mass., USA). In some cases, embolic microspheres may include a therapeutic agent, such as a small molecule pharmaceutical agent (i.e. a drug), permitting concurrent vessel embolization and delivery of the drug to the vicinity of the embolized vessel. In one specific instance, a therapeutic agent (doxorubicin) has been directly added to polyvinyl alcohol hydrogel microspheres such that it can be released locally after delivery (the DC Bead™ drug delivery chemoembolization system, Biocompatibles International plc, Farnham, Surrey, UK). Other examples of commercially available microspheres include glass microspheres with entrapped radioisotopes such as $^{90}Y$ (TheraSpheres™, MDS Nordion, Ottowa, Canada) and polymer microspheres that contain monomers that are capable of chelating radioisotopes including $^{90}Y$ (SIR-Spheres®, SIR-Tex Medical, New South Wales, Australia).

While drug-loaded microspheres have a number of useful characteristics, they also have several limitations. For instance, commercially available drug eluting microspheres are generally biostable, and tend to remain in place even after they have delivered most of their drug preloads. And, they deliver those drug preloads relatively quickly: in vitro testing of currently available drug eluting microspheres loaded with chemotherapeutics shows that these microspheres release all or most of their drug payload in a single burst within about five hours; this rapid drug release may result in brief but high systemic dosing in cases where extended, local dosing is desired. In addition, drug eluting microspheres currently sold are not necessarily shelf-stable, and must be loaded with drug shortly before they are used. Finally, currently approved microsphere products are generally limited to delivering cationic drugs, meaning only a narrow subset of chemotherapeutics—doxorubicin and irinotecan—are compatible with currently-used microspheres.

SUMMARY OF THE INVENTION

The present invention, in its various aspects, addresses the shortcomings of existing drug eluting microspheres for embolization by providing poly(lactide-co-glycolide) (PLGA) microspheres which degrade over intervals ranging from about 1 month to about one year and which elute drug over intervals ranging from 2-4 weeks to one or more months. The microspheres are preferably loaded with a lipophilic drug such as paclitaxel ("Ptx"), which is added to the PLGA polymer phase during manufacture of the particles, and which are shelf-stable for a period of months prior to use.

In one aspect, the present invention relates to a polymer microsphere which comprises (or in some cases consists essentially of) PLGA 50:50 and Ptx, in which both the PLGA and the PTX are distributed substantially evenly (i.e. their concentrations are approximately the same throughout the microsphere). The polymer microsphere can have a smooth surface, and may comprise PLGA having an average molecular weight of 5,600, 16,000 or 8300 Daltons. Ptx may be released in vitro from the microsphere in a variety of ways including over a period of approximately 3 weeks, in an initial burst over about two days or less and/or as a steady state process over 15-20 days. The microsphere can be formed, in some cases, by an emulsion process in which Ptx and PLGA are co-emulsified in an organic phase. The microsphere, which can contain 5-10% Ptx by weight (i.e. they can contain 5 wt % Ptx, 10 wt % Ptx, or any value therebetween), may be used in some cases for the treatment of tumors, for example hepatocellular carcinoma, and may be a part of a kit, in which case it is disposed in a vessel with a gas such as argon or nitrogen and optionally packaged with a syringe having a bore sized to permit the inflow of the polymer microsphere. Kits of the present invention (which can utilize microspheres having any combination of the features described above) can also include a written set of instructions for performing a method that includes the step of placing the polymer microsphere within a body lumen.

In another aspect, the present invention relates to a method of treating a patient that includes the step of placing a polymer microsphere which comprises (or in some cases consists essentially of) PLGA 50:50 and Ptx into a body lumen of a patient, which lumen can be (among other things) a blood vessel which provides blood to a hepatocellular carcinoma. The polymer microsphere can be delivered, for example, by flowing it in a fluid suspension through a catheter and into the blood vessel, and the method can also include a step of fluroscopically imaging the polymer microsphere within the blood vessel, and/or at least partially occluding the blood vessel.

DRAWINGS

Aspects of the invention are described below with reference to the following drawings in which like numerals reference like elements, and wherein.

Figure 1:
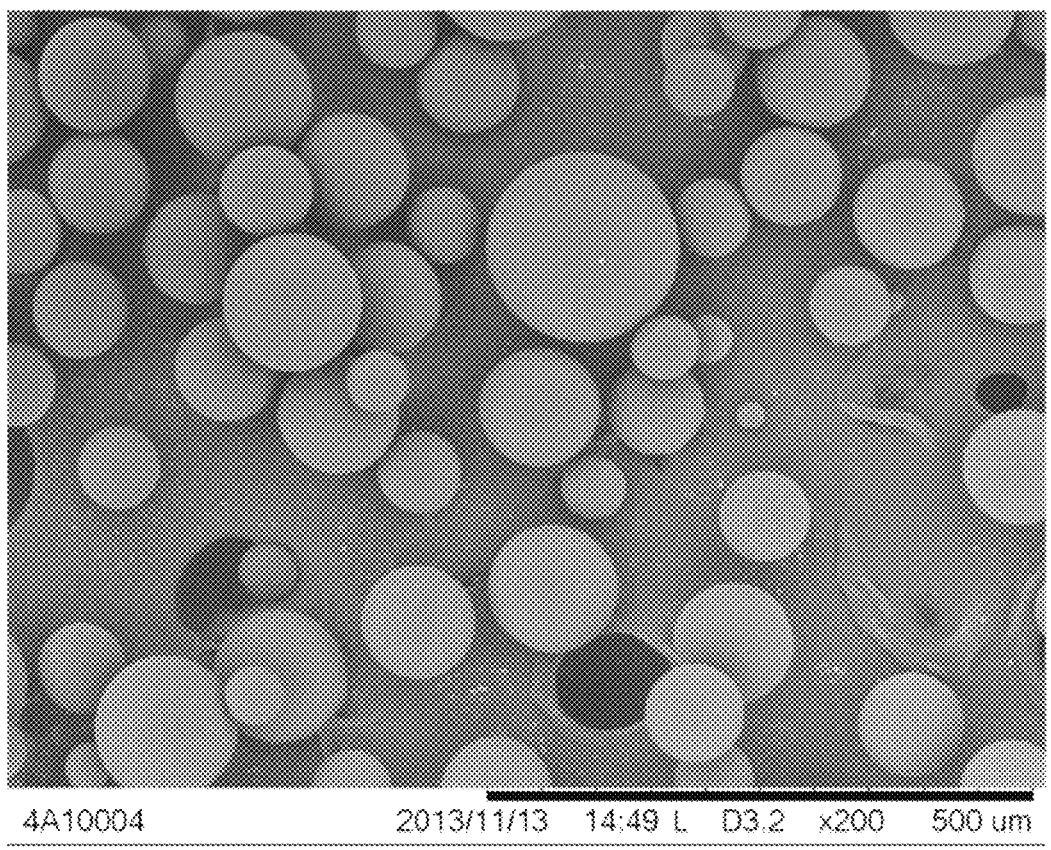
FIG. 1 shows a scanning electron micrograph (SEM) of drug eluting microspheres according to an embodiment of the present invention.

Unless otherwise provided in the following specification, the drawings are not necessarily to scale, with emphasis being placed on illustration of the principles of the invention.

DETAILED DESCRIPTION OF THE PREFERRED EMBODIMENTS

Microspheres Generally:

Drug eluting microspheres as disclosed in the present invention are based on biocompatible, hydrophilic, and non-toxic polymers. The microspheres can be any suitable size or shape depending on their desired use, though in preferred embodiments the microspheres are characterized by one or more of the following features: they are injectable through a needle of 18 gauge or smaller, they are generally spherical, and are capable of eroding, hydrolyzing, and/or otherwise being resorbed or degraded by endogenous processes such as phagocytosis.

While preferred embodiments of the present invention utilize PLGA 50:50, any suitable polymer or copolymer composition can be used (including, without limitation, PLGA 85:15, 75:25, 50;50 and poly-lactic acid ("PLA") containing compositions), subject to the following preferences: first, the polymer is preferably capable of forming microspheres using an emulsion process; second, the polymer is preferably one in which a therapeutic agent such as a small molecule drug is compatible; and third, the polymer is preferably biocompatible. Preferred polymers are typically hydrophobic, to facilitate their extended residence and release of drug within the body.

Drug eluting microspheres according to the various embodiments of the present invention have drug release kinetics that can be varied somewhat during the manufacturing process by changing one or more variables of production, including (1) the average molecular weight of the PLGA polymer used, (2) the amount of drug initially loaded into the particles during manufacture (which may be expressed as a fraction of the total mass of the polymer phase used to generate the microspheres; i.e. a wt %), and (3) the size of the particles (small particles generally having a greater surface area-to volume, thereby permitting more rapid diffusion of drug out of the particle). The release of drug also generally varies with the rate of degradation of the polymer, as a more rapid rate of degradation will tend to result in a more rapid release of drug. In general, the greater the proportion of glycolide to lactide, the more rapid the degradation of the microspheres and, hence, the more rapid the release of drug. In addition, drug release rates can be modified by the inclusion of excipients such as polyvinylpyrrolidone ("PVP").

In use, microspheres and embolic compositions of the present invention are used to embolize and optionally deliver drug to any structure or region in which embolization and drug therapy is desired. In some cases, the microspheres do not include any therapeutic agent, and are simply used to embolize a solid tumor or growth in the liver, uterus, prostate, kidney, etc. For instance, PLGA microspheres of the present invention, without any drug loading, may be used to embolize part or all of the prostate in order to treat benign prostatic hyperplasia.

In preferred embodiments, however, PLGA/Ptx microspheres are used to embolize and deliver Ptx to a heptatocellular carcinoma or another tumor growing in the liver. In other cases, the microspheres (loaded with Ptx or another drug) are used to treat one or more other solid tumor types in a different region, such as the mouth and/or neck, kidney, pancreas, breast, lung, and prostate. In these cases, the size and drug loading can be tailored to the tumor type and location.

Finally, in addition to treatment of various cancers with chemotherapeutic or antiproliferative drugs, microspheres of the present invention can be loaded with any other therapeutic agents such as analgesics for the localized delivery of pain medications. Other drugs that can be loaded into microspheres of the present invention include, without limitation, ketorolac, tamsulosin, everolimus and sorafenib.

EXAMPLES

The principles of the invention are further illustrated In the following non-limiting examples:

Example 1

Preparation of PLGA/Ptx Beads

A single emulsion method can be used for PLGA/Ptx microsphere preparation. PLGA and Ptx were first dissolved into dichloromethane solvent with 10-30% concentration, then this solution was added to 0.2% PVA aqueous solution with appropriate agitation to form a "liquid droplet". This liquid droplet was transferred subsequently to 0.02% PVA-in-water solution to further "harden" the microspheres by removing the dichloromethane solvent from the polymer phase; the hardening step lasts for a few (e.g. 2-6) hours, and is followed by a wash with water to remove PVA before the microspheres are dried under vacuum at room temperature overnight (e.g. 10-14 hours). The resulting microspheres were comprised predominantly (i.e. essentially) of PLGA and Ptx. Their size distribution ranged from 50 micron to 250 micron. The drug loadings within microsphere can change from 0 to 90% depending on the polymer to drug ratio used in the formulation. PLGA being used for microsphere formations include PLGA 50:50, PLGA 75:25, and PLGA 85:15 with various molecular weights. FIG. 1 shows a scanning electron microscope (SEM) image of PLGA/Ptx microsphere.

Example 2

Drug Release Profile of PLGA/Ptx Beads

Figure 2:
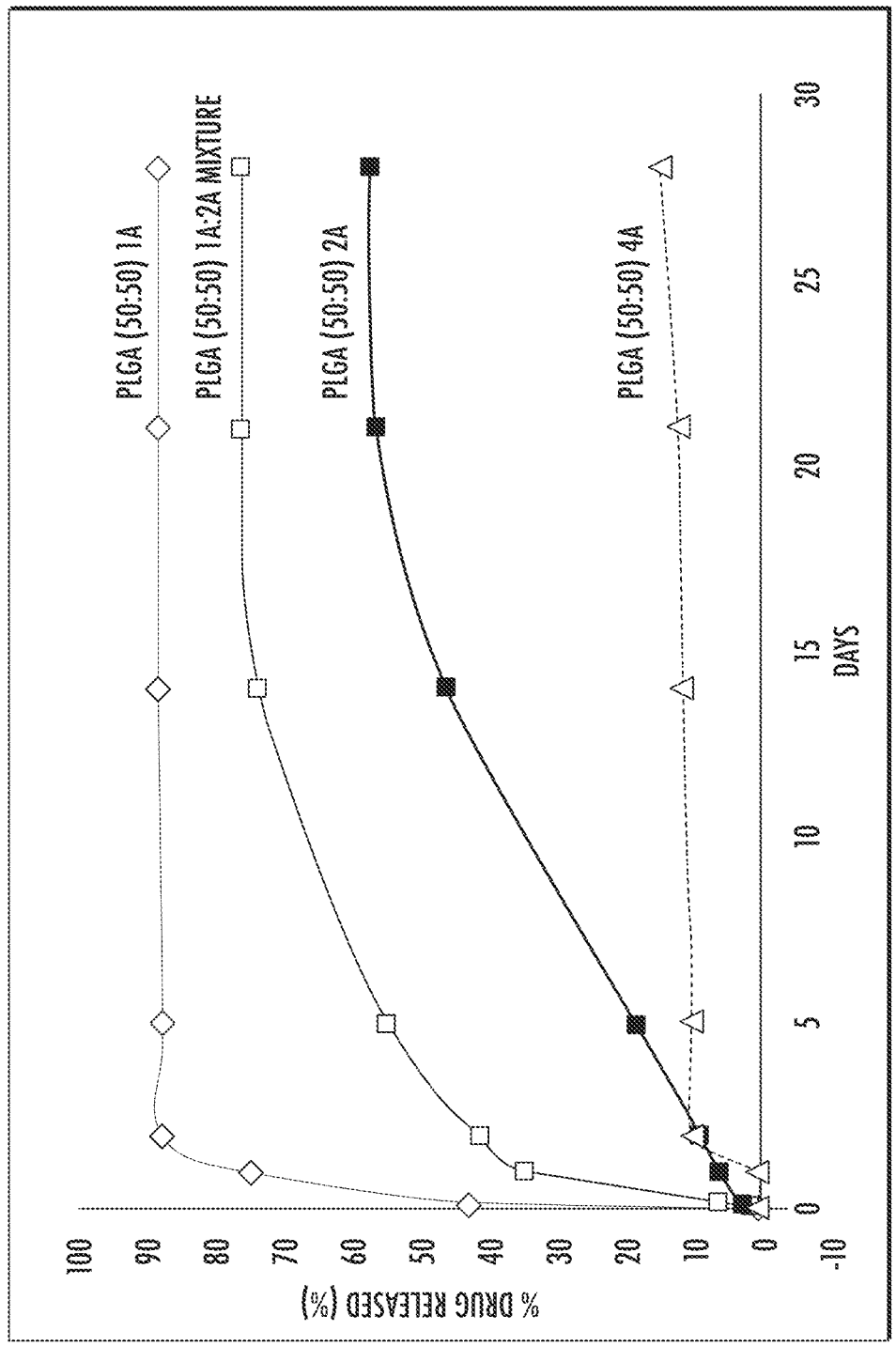
FIG. 2 shows in vitro drug elution profiles of microspheres according to the present invention which incorporate 50:50 PLGA polymer phases having an average molecular weights of 5,600 Da ("1 A"), 16,000 Da ("2 A") or 50,000 Da ("4 A").

To show that the drug release profile and duration of microspheres of the present invention can be adjusted, in vitro drug elution of microspheres formed with different molecular weight grades of PLGA, (1 A, 2 A and 4 A) was measured. The impact of different grades of PLGA on drug release profiles is summarized in FIG. 2, which shows that, while microspheres made from different grades of PLGA are all characterized by some degree of burst-release and steady-state release, the quantity of drug released by the microspheres (as a wt %) at a given timepoint tends to decrease as the molecular weight of the PLGA used increases. This decrease affects both the initial burst of drug release as well as the slower, steady-state drug release that follows. As the figure shows, very little drug elutes from microspheres formed with 4 A PLGA, while almost all of the drug content in 1 A microspheres elutes in a single rapid burst. Interestingly, the microspheres formed from 2 A PLGA had a relatively small degree of burst release but a long period (~20 days) of steady-state release, while microspheres made of a 50/50 mix of 1 A and 2 A were characterized by both burst release and about 15 days of steady-state release.

Example 3

In Vivo Embolization and Drug Effect in Animal Study

Figure 3A:
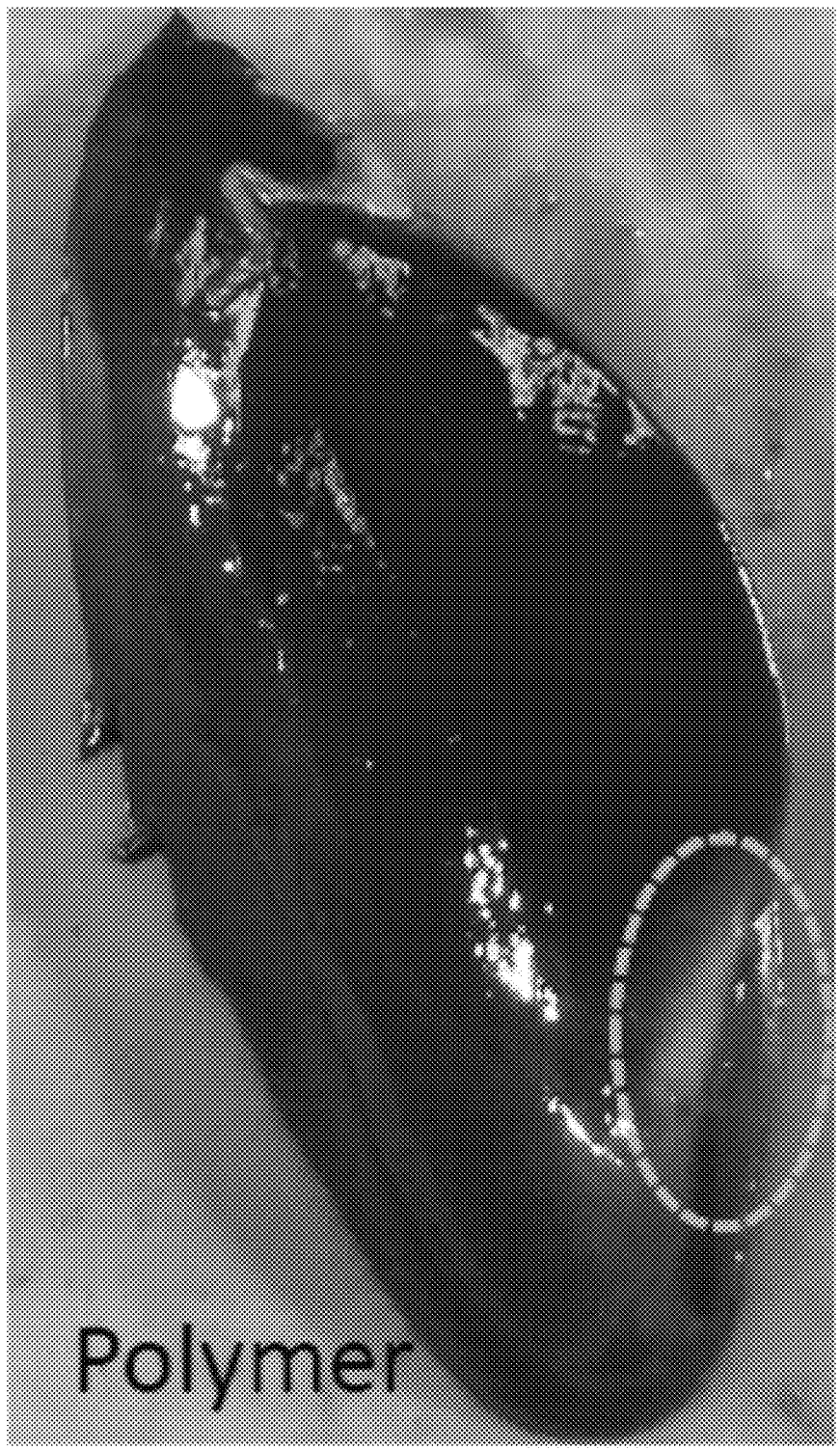
FIGS. 3A through 3C show the effects of embolization of swine kidney using drug eluting microspheres of the present invention comprising polymer only (FIG. 3A), polymer and 5% paclitaxel (FIG. 3B) or 10% paclitaxel (FIG. 3C).
Figure 3B:
Figure 3C:
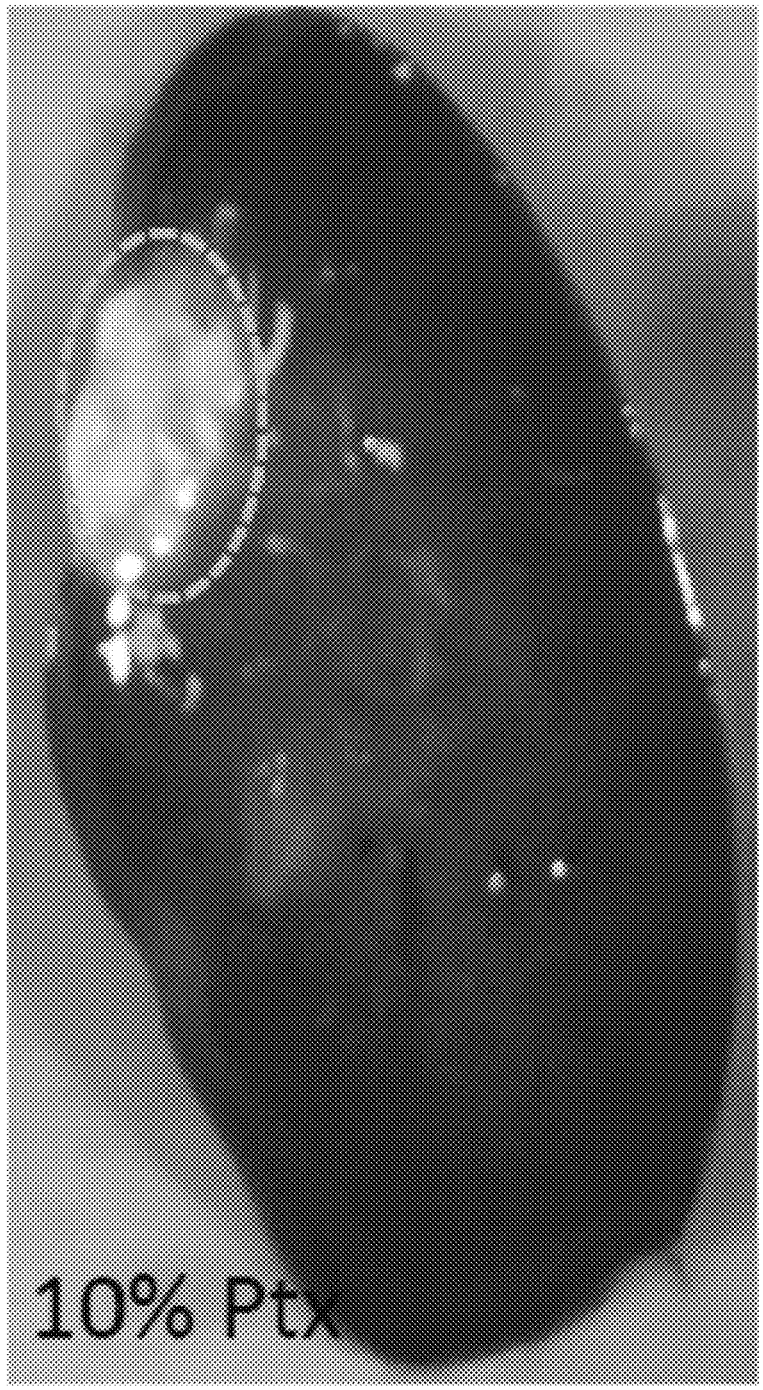

Polymer only microsphere (PLGA 50:50 4 A) and drug loading microsphere (5% and 10% drug loading in PLGA 50:50 1 A:2 A mixture formulation) were injected into swine kidneys to assess their effects in vivo. The kidneys were explanted at 30 days to investigate gross effect of beads embolization and drug effects. FIGS. 3A-C demonstrate that all three microsphere compositions caused some degree of necrosis, but the 5% and 10% Ptx loaded beads showed, at least qualitatively, a greater degree of necrosis than the polymer-only microspheres.

Example 4

Preparation and Evaluation of Radiopaque Beads

Figure 4A:
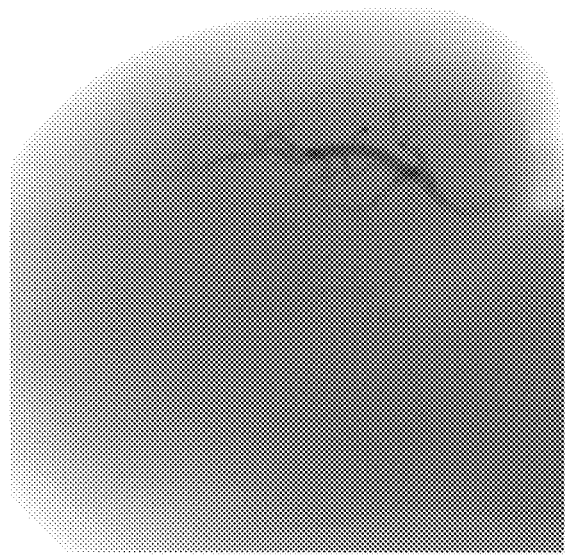
FIGS. 4A and 4B show low magnification (FIG. 4A) and high-magnification (FIG. 4B) computerized tomography ("CT") images of radiopaque drug eluting microspheres according to the present invention.
Figure 4B:
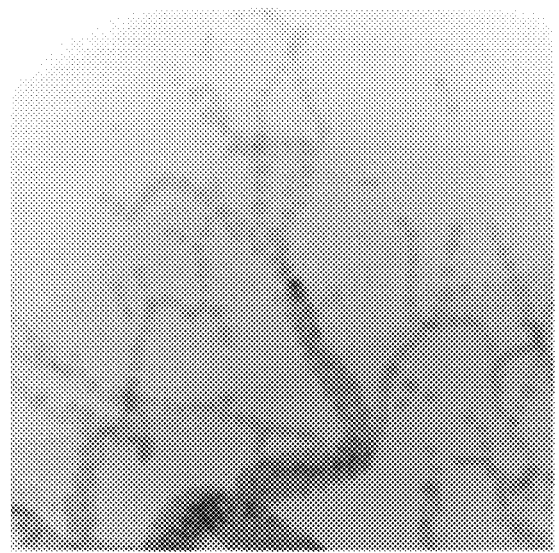

Beads were prepared as described in Example 1 with the exception that lipiodol was dissolved in DCM along with PLGA to give a lipiodol loading in the beads of ~40% (wt/wt). The beads were injected into porcine liver and kidney and imaged post mortem using 2D CT. FIG. 4 shows CT image of beads in the kidney. As the image shows, the microspheres are readily visible and appear to fully occlude the blood vessels in which they have been deposited.

The phrase "and/or," as used herein should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

The term "consists essentially of" means excluding other materials that contribute to function, unless otherwise defined herein. Nonetheless, such other materials may be present, collectively or individually, in trace amounts.

As used in this specification, the term "substantially" or "approximately" means plus or minus 10% (e.g., by weight or by volume), and in some embodiments, plus or minus 5%. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

Certain embodiments of the present invention have described above. It is, however, expressly noted that the present invention is not limited to those embodiments, but rather the intention is that additions and modifications to what was expressly described herein are also included within the scope of the invention. Moreover, it is to be understood that the features of the various embodiments described herein were not mutually exclusive and can exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. As such, the invention is not to be defined only by the preceding illustrative description.

The invention claimed is:

1. A method of treating a patient, the method comprising: placing, within a blood vessel of a tumor of the patient, polymer microspheres consisting essentially of poly-lactide-co-glycolide 50:50 and 5-10 wt % therapeutic agent such that the blood vessel is embolized.

2. The method of claim 1, wherein the body lumen is a blood vessel which provides blood to a hepatocellular carcinoma.

3. The method of claim 2, wherein the step of placing the polymer microspheres within the body lumen includes flowing a fluid suspension including the polymer microspheres through a catheter and into the blood vessel.

4. The method of claim 3, further comprising the step of fluoroscopically imaging the polymer microspheres within the blood vessel, and wherein the polymer microspheres includes a contrast agent.

5. A method of treating a patient, the method comprising: placing, within a body lumen of the patient, a polymer microsphere consisting essentially of poly-lactide-co-glycolide 50:50 and 5-10 wt % therapeutic agent, wherein the body lumen is a blood vessel which provides blood to a hepatocellular carcinoma, and wherein the step of placing the polymer microsphere in the body lumen includes at least partially occluding the blood vessel.

6. A method of treating a patient, the method comprising: placing polymer microspheres within a blood vessel of the patient, such that the blood vessel is embolized, the microspheres consisting essentially of poly-lactide-co-glycolide 50:50 (PLGA) and paclitaxel (Ptx), both being distributed throughout the microspheres, and configured to release Ptx in vitro in an initial burst lasting no more than approximately two days, followed by a steady-state release lasting approximately 15-20 days.

7. The method of claim 6, wherein the blood vessel is a blood vessel of a tumor.

8. The method of claim 6, wherein the blood vessel provides blood to a hepatocellular carcinoma.

9. The method of claim 7, wherein the step of placing the polymer microspheres within the body lumen includes flowing a fluid suspension including the polymer microspheres through a catheter and into the blood vessel.

10. The method of claim 9, further comprising the step of fluoroscopically imaging the polymer microspheres within the blood vessel, and wherein the polymer microspheres includes a contrast agent.

11. The method of claim 5, wherein the step of placing the polymer microspheres within the body lumen includes flowing a fluid suspension including the polymer microspheres through a catheter and into the blood vessel.

12. The method of claim 11, further comprising the step of fluoroscopically imaging the polymer microspheres within the blood vessel, and wherein the polymer microspheres includes a contrast agent.

* * * * *